US012731257B2

(12) United States Patent
Ko

(10) Patent No.: US 12,731,257 B2
(45) Date of Patent: Sep. 8, 2026

(54) SYSTEM AND METHOD FOR PERFORMING CANCER DIAGNOSIS WITH INCOMPLETE SET OF CT IMAGES

(71) Applicant: MedAI CO., LTD., Seoul (KR)

(72) Inventor: Sung-Jea Ko, Seoul (KR)

(73) Assignee: MedAI CO., LTD., Seoul (KR)

( * ) Notice: Subject to any disclaimer, the term of this patent is extended or adjusted under 35 U.S.C. 154(b) by 324 days.

(21) Appl. No.: 18/596,619

(22) Filed: Mar. 5, 2024

(65) Prior Publication Data

US 2025/0078274 A1 Mar. 6, 2025

(30) Foreign Application Priority Data

Sep. 6, 2023 (KR) ........................ 10-2023-0118333

(51) Int. Cl.

| | |
|---|---|
| ***G06T 7/00*** | (2017.01) |
| ***A61B 6/00*** | (2024.01) |
| ***G06V 10/26*** | (2022.01) |
| ***G06V 10/764*** | (2022.01) |
| ***G06V 10/77*** | (2022.01) |
| ***G06V 10/80*** | (2022.01) |
| ***G06V 10/82*** | (2022.01) |

(52) U.S. Cl.
CPC .......... *G06T 7/0014* (2013.01); *A61B 6/5217* (2013.01); *G06V 10/26* (2022.01); *G06V 10/764* (2022.01); *G06V 10/7715* (2022.01); *G06V 10/806* (2022.01); *G06V 10/82* (2022.01); *G06T 2207/10081* (2013.01); *G06T 2207/20084* (2013.01); *G06T 2207/30096* (2013.01)

(58) Field of Classification Search
CPC ......... G06T 7/0014; G06T 2207/10081; G06T 2207/20084; G06T 2207/30096; G06V 10/806; G06V 10/7715; G06V 10/82; G06V 10/26; G06V 10/764; A61B 6/5217
See application file for complete search history.

(56) References Cited

FOREIGN PATENT DOCUMENTS

| | | | |
|---|---|---|---|
| KR | 10-2019-0132296 | A | 11/2019 |
| KR | 10-2020-0038360 | A | 4/2020 |
| KR | 10-2100699 | B1 | 4/2020 |

(Continued)

OTHER PUBLICATIONS

Patel, Dhruv V. et al., "Probabilistic recovery of missing images in contrast-enhanced CT," Fourth Workshop on Medical imaging meets NeurIPS (NeurIPS 2020), Online.

*Primary Examiner* — Mark Roz
(74) *Attorney, Agent, or Firm* — Bridgeway IP Law Group, PLLC; Sang Ho Lee; Hyun Woo Shin

(57) ABSTRACT

A cancer diagnosis system that performs cancer diagnosis from an incomplete set of CT images having at least one missing phase includes an input unit that receives the incomplete set of CT images, a full-phase CT image set generation unit that synthesizes CT images for the at least one missing phase to generate a full-phase CT image set, a lesion-level feature extraction unit that extracts a feature map and a segmentation map from the full-phase CT image set, and extracts lesion-level features from the feature map and the segmentation map, and a cancer subtype prediction unit that predicts a subtype of cancer based on the extracted lesion-level features. Therefore, it may be possible to synthesize CT images with missing phases, and perform accurate classification of the pathological subtype of the tumor in consideration of the synthesized CT images.

6 Claims, 6 Drawing Sheets

(56) References Cited

FOREIGN PATENT DOCUMENTS

| | | | |
|---|---|---|---|
| KR | 10-2020-0066732 | A | 6/2020 |
| KR | 10-2166441 | B1 | 10/2020 |
| KR | 10-2022-0041720 | A | 4/2022 |
| KR | 10-2428725 | B1 | 8/2022 |

| Classifier input | Method | mAUC | *p*-value |
|---|---|---|---|
| Tree-phase | Cls-3P | 78.1 | 0.0227 |
| Tree-phase + One synthesized | BaseSyn | 77.8 | 0.0053 |
| | CollaGAN | 77.3 | 0.0049 |
| | Syn-Seg | 77.9 | 0.0080 |
| | ReMIC | 77.7 | 0.0029 |
| | DiagnosisGAN | **79.6** | - |

FIG. 6A

| Classifier input | Method | mAUC |
|---|---|---|
| Two-phase | Cls-2P | 79.8 |
| Two-phase + Two synthesized | BaseSyn | 77.2 |
| | Syn-Seg | 77.6 |
| | ReMIC | 75.4 |
| | DiagnosisGAN | **81.6** |

FIG. 6B

SYSTEM AND METHOD FOR PERFORMING CANCER DIAGNOSIS WITH INCOMPLETE SET OF CT IMAGES

CROSS-REFERENCE TO RELATED APPLICATION

This application claims priority to and the benefit of Korean Patent Application No. 10-2023-0118333 filed on Sep. 6, 2023, the entire contents of which are incorporated herein by reference.

BACKGROUND OF THE INVENTION

Field of the Invention

The present disclosure relates to the field of cancer diagnosis, and more particularly, to a system and method for performing cancer diagnosis from an incomplete set of CT images.

Background of the Related Art

Cancer subtype classification is very important in patient management because cancer treatment planning and prognosis prediction depend on the pathological subtype of the tumor.

Medical images may be used to classify cancer subtypes, and medical images may allow a non-invasive diagnosis of cancer, thereby preventing unnecessary biopsies or surgeries.

In particular, multi-modal medical images may provide complementary visual information on a lesion so as to be used to accurately diagnose a patient, and the multi-modal medical images include computed tomography (CT) images and magnetic resonance imaging (MRI) images.

Computed tomography (CT) images, which are images obtained by capturing a series of CT volumes before and after contrast agent injection, consist of dynamic contrast-enhanced computed tomography images with four different phases to be mainly used for the differentiation and diagnosis of cancer.

Magnetic resonance imaging (MRI) images, which are multi-parametric magnetic resonance imaging images, may be mainly used to diagnose brain diseases.

However, the multi-modal medical images have difficulties in acquiring a complete set of images with all modalities due to different imaging protocols and acquisition costs, image damage, and patient characteristics among medical institutions.

In particular, problems such as discomfort in movement due to breathing, allergic reactions to contrast agents, scanner system errors, and the like may cause missing phases in the multi-modal medical images.

Meanwhile, for accurate cancer diagnosis, it is necessary to acquire CT images with at least four phases. However, a normal CT scan may only acquire CT images with two or three phases. Therefore, a method of repeating the CT scan for an accurate cancer diagnosis may be taken into consideration, but because of additional cost and radiation exposure due to repeating the CT scan, cancer diagnosis is generally made using only the CT images with available phases.

However, for more accurate preoperative cancer differentiation and diagnosis, it is necessary to acquire CT images with more phases, and thus there is a need to recover CT images with missing phases and differentiate and diagnose cancer through the recovered CT images without repeating the CT scan.

SUMMARY OF THE INVENTION

The present disclosure aims to provide a system and method for performing cancer diagnosis with incomplete CT images.

The problems of the present disclosure are not limited to the above-mentioned problems, and other problems which are not mentioned herein will be clearly understood by those skilled in the art from the description below.

A cancer diagnosis system according to an embodiment of the present disclosure, which is a cancer diagnosis system that performs cancer diagnosis from an incomplete set of CT images having at least one missing phase, the cancer diagnosis system, including an input unit that receives the incomplete set of CT images, a full-phase CT image set generation unit that synthesizes the CT images with missing phases to generate a full-phase CT image set, a lesion-level feature extraction unit that extracts a feature map and a segmentation map from the full-phase CT image set, and extracts lesion-level features from the feature map and the segmentation map, and a cancer subtype prediction unit that predicts a subtype of cancer based on the lesion-level features.

A cancer diagnosis method according to another embodiment of the present disclosure, which is a cancer diagnosis method that performs cancer diagnosis from an incomplete set of CT images having at least one missing phase, the cancer diagnosis method, including receiving, by an input unit, the incomplete set of CT images, synthesizing, by a full-phase CT image set generation unit, the CT images with missing phases to generate a full-phase CT image set, extracting, by a lesion-level feature phase unit, a feature map and a segmentation map from the full-phase CT image set, and extracting lesion-level features from the feature map and the segmentation map, and predicting, by a cancer subtype prediction unit, a subtype of cancer based on the lesion-level features.

According to an integrated system and method for performing cancer diagnosis with incomplete CT images according to the present disclosure, CT images with missing phases may be additionally generated and synthesized to perform accurate classification of the pathological subtype of the tumor in consideration of the additionally generated CT images.

The integrated system and method for performing cancer diagnosis with incomplete CT images according to the present disclosure may perform cancer subtype classification using additionally generated CT images, thereby having an effect of improving performance compared to classification using incomplete data.

However, the effects of the present disclosure are not limited to the above-mentioned effect, and other effects that are not mentioned herein will be clearly understood by those skilled in the art from the description below.

BRIEF DESCRIPTION OF THE DRAWINGS

FIGS. 6A and 6B are tables showing quantitative comparison results of cancer subtype classification performances.

DETAILED DESCRIPTION OF THE PREFERRED EMBODIMENT

Figure 1:
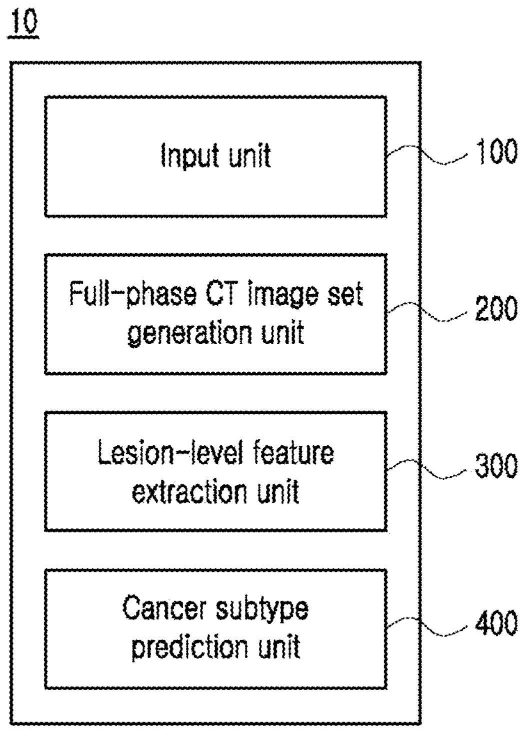
FIG. 1 is a block diagram showing a cancer diagnosis system according to an embodiment of the present disclosure.

Advantages and features of the present disclosure, and methods of accomplishing the same will be clearly understood with reference to the following embodiments described below in detail in conjunction with the accompanying drawings. However, the present disclosure is not limited to those embodiments disclosed below but may be implemented in various different forms. It should be noted that the present embodiments are merely provided to make a full disclosure of the invention and also to allow those skilled in the art to know the full range of the invention, and therefore, the present disclosure is to be defined only by the scope of the appended claims. Throughout the specification, the same reference numerals represent the same elements.

Embodiments described herein will be description with reference to cross-sectional views and/or plan views, which are ideal exemplary views of the present disclosure. In the drawings, the thicknesses of the components are exaggerated for effective description of technical content. Therefore, the components illustrated in the drawings have schematic properties, and the shapes of the components illustrated in the drawings are intended to illustrate specific forms thereof and are not intended to limit the scope of the disclosure. In various embodiments of the present specification, terms such as first, second, and third are used to describe various elements, but these elements should not be limited by these terms. The terms are used merely for the purpose to distinguish an element from the other element. Embodiments described and illustrated herein also include complementary embodiments thereof.

It should be noted that the terms used herein are merely used to describe the embodiments, but not to limit the present disclosure. In this specification, unless clearly used otherwise, expressions in a singular form include a plural form. The term "comprises" and/or "comprising" used in the specification intend to express a constituent element, a step, an operation and/or a device does not exclude the existence or addition of one or more other constituent elements, steps, operations and/or devices.

Unless otherwise defined, all terms (including technical and scientific terms) used in this specification may be used with meanings that can be commonly understood by those skilled in the art to which the present disclosure pertains. Additionally, terms defined in commonly used dictionaries are not interpreted ideally or excessively unless clearly specifically defined.

The term "unit" or "module" are defined herein as having its broadest definition to ordinary skill in the art, including software including instructions executable in a non-transitory computer-readable medium that would perform the associated function when executed, a circuit designed to perform the associated function, hardware designed to perform the associated function, or a combination of software, a circuit, or hardware designed to perform the associated function.

Further, it is to be understood that all detailed descriptions mentioning specific embodiments of the present disclosure as well as principles, aspects, and embodiments of the present disclosure are intended to include structural and functional equivalences thereof. Further, it is to be understood that these equivalences include an equivalence that will be developed in the future as well as an equivalence that is currently well-known, that is, all elements invented so as to perform the same function regardless of a structure.

Therefore, it is to be understood that, for example, block diagrams of the present specification illustrate a conceptual aspect of an illustrative circuit for embodying a principle of the present disclosure. Therefore, it is to be understood that all flow charts, state transition diagrams, pseudo-codes, and the like, illustrate various processes that may be tangibly embodied in a computer-readable medium and that are executed by computers or processors regardless of whether or not the computers or the processors are clearly illustrated.

Functions of various elements including processors or functional blocks represented as concepts similar to the processors and illustrated in the accompanying drawings may be provided using hardware having capability to execute software in connection with appropriate software as well as dedicated hardware. When the functions are provided by the processors, they may be provided by a single dedicated processor, a single shared processor, or a plurality of individual processors, and some of them may be shared with each other.

In addition, the explicit use of terms presented as the processor, control, or similar concepts should not be interpreted exclusively by quoting hardware capable of executing software, but should be understood to implicitly include, without limitation, digital signal processor (DSP) hardware, a ROM for storing software, a RAM, and a non-volatile memory. The above-mentioned terms may also include well-known other hardware.

In the claims of the present specification, components represented as means for performing functions mentioned in a detailed description are intended to include all methods for performing functions including all types of software including, for example, a combination of circuit devices performing these functions, firmware/micro codes, or the like, and are coupled to appropriate circuits for executing the software so as to execute these functions. It is to be understood that since functions provided by variously mentioned means are combined with each other and are combined with a method demanded by the claims in the present disclosure defined by the claims, any means capable of providing these functions are equivalent to means recognized from the present specification.

Hereinafter, with reference to the drawings, the concept of the present disclosure and embodiments thereof will be described in detail.

Figure 2:
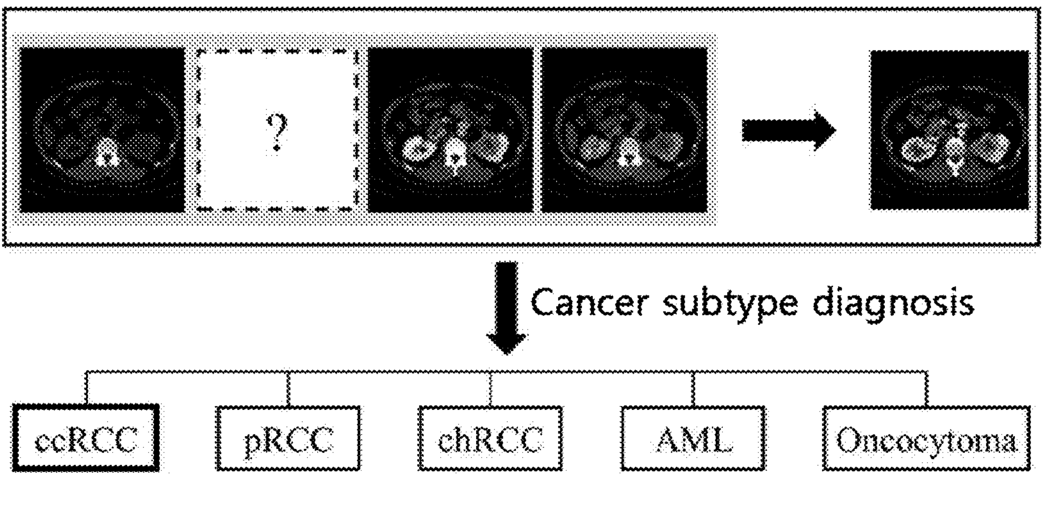
FIG. 2 is a diagram illustrating a concept of an integrated framework of the cancer diagnosis system shown in FIG. 1.
Figure 3:
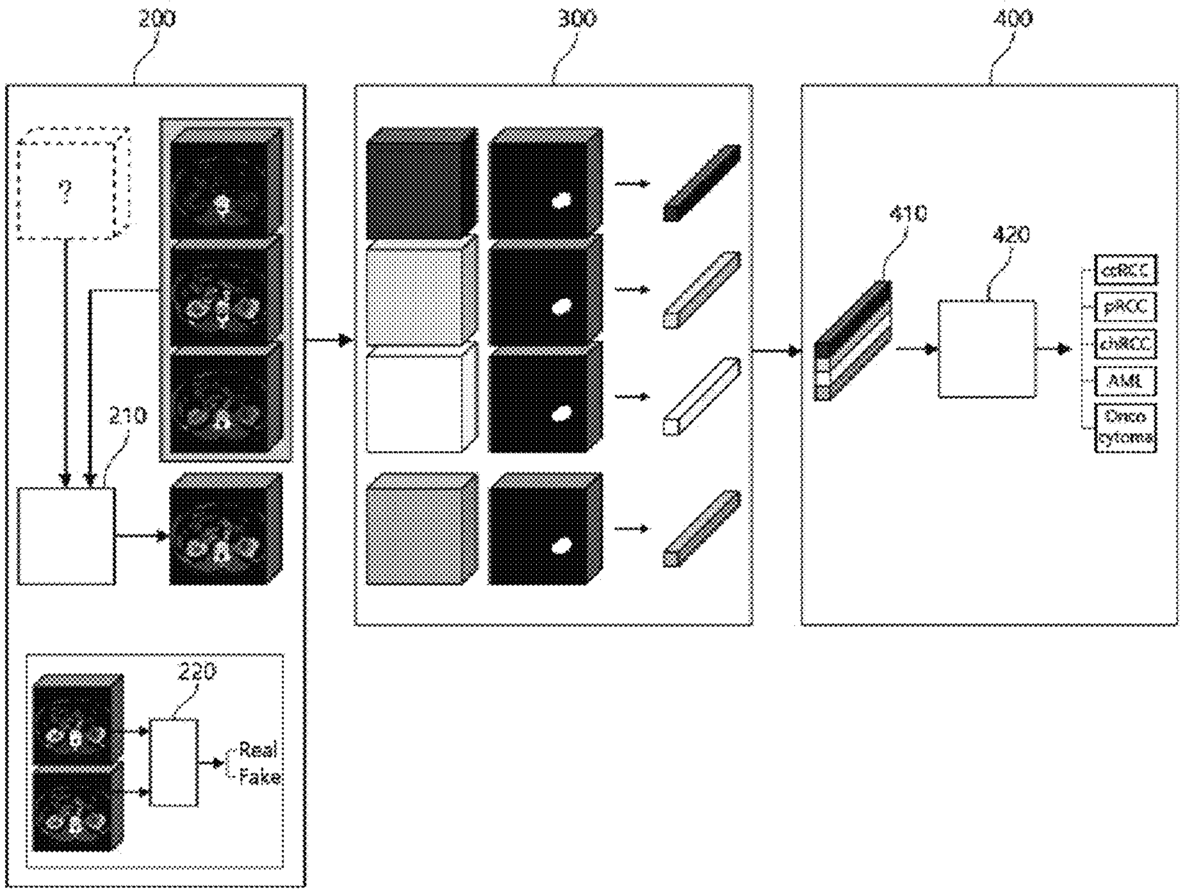
FIG. 3 is a diagram conceptually showing an operation of each component of the cancer diagnosis system shown in FIG. 1.
Figure 4:
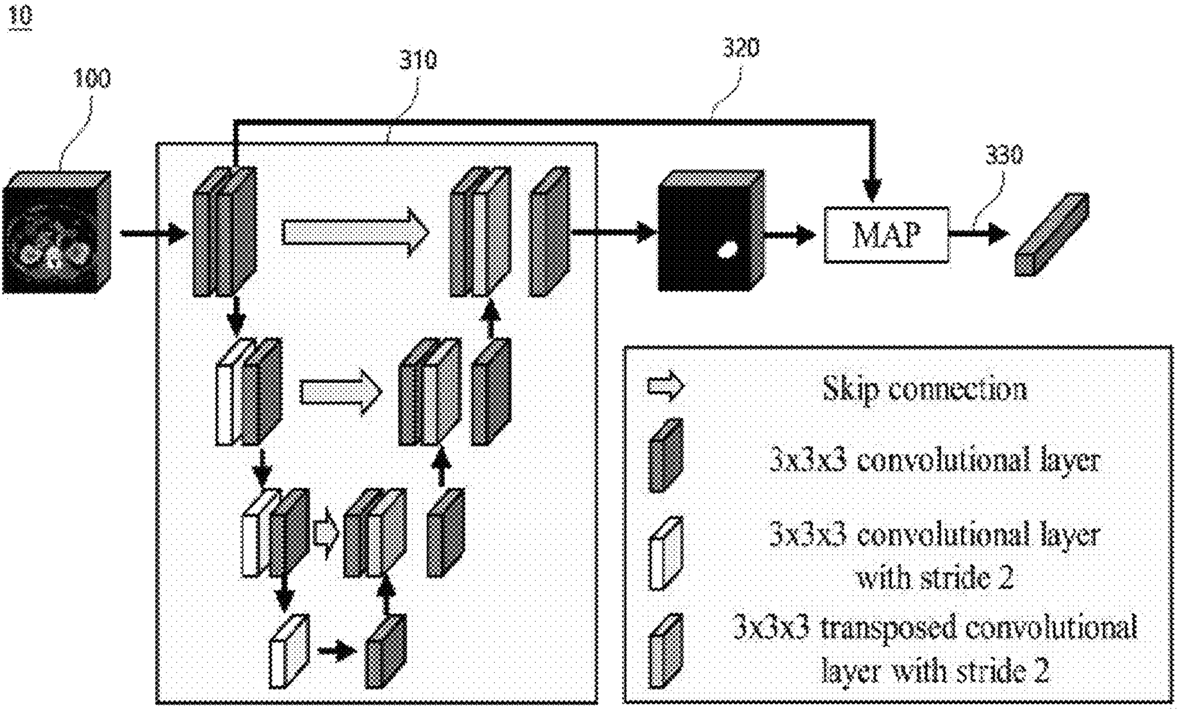
FIG. 4 is a diagram showing in detail a lesion-level feature extraction unit shown in FIG. 1.

FIG. 1 is a block diagram showing a cancer diagnosis system according to an embodiment of the present disclosure, FIG. 2 is a diagram illustrating a concept of an integrated framework of the cancer diagnosis system shown in FIG. 1, FIG. 3 is a diagram conceptually showing an operation of each component of the cancer diagnosis system shown in FIG. 1, and FIG. 4 is a diagram showing in detail a lesion-level feature extraction unit shown in FIG. 1.

A cancer diagnosis system 10 according to this embodiment performs cancer diagnosis from an incomplete set of CT images.

As shown in FIG. 2, the cancer diagnosis system 10 is configured with a framework based on a generative adversarial network (GAN) for synthesis of diagnostic information images to implement synthesis of missing CT phases and cancer subtype classification in a single framework.

More specifically, the cancer diagnosis system 10 according to this embodiment may synthesize missing phases from an incomplete set of CT images having at least one missing phase to implement a full-phase CT image set, which is a complete set of CT images.

Additionally, the cancer diagnosis system 10 according to this embodiment may predict a subtype of cancer from the full-phase CT image set. For example, the predicted subtype of the cancer may be any one of renal cancer subtypes, such as clear cell renal cell carcinoma (ccRCC), papillary renal cell carcinoma (pRCC), chromophobe renal cell carcinoma (chRCC), angiomyolipoma (AML), and oncocytoma, but is not limited thereto.

The system 10 may be implemented as at least one device that may be mobile or fixed. Here, the device may be in the form of a server or engine, and may be referred to as other terms such as a device, an apparatus, a terminal, a user equipment (UE), a mobile station (MS), a wireless device, a handheld device, and the like.

Hereinafter, each component of the cancer diagnosis system 10 will be mainly described.

As shown in FIG. 1, the cancer diagnosis system 10 according to this embodiment includes an input unit 100, a full-phase CT image set generation unit 200, a lesion-level feature extraction unit 300, and a cancer subtype prediction unit 400. The input unit 100, the full-phase CT image set generation unit 200, the lesion-level feature extraction unit 300, and the cancer subtype prediction unit 400 may be controlled by software for performing a cancer diagnosis method executed in the cancer diagnosis system 10, and each component may be implemented as a separate device or as a partial module of the device.

The input unit 100 receives a set of CT images for diagnosing cancer as input data.

Here, the CT image set, which is an image actually taken of a body part for which cancer is to be diagnosed, for example, may be an image from among a non-contrast phase, an arterial phase, a portal phase, and a delayed phase. Here, the arterial phase may refer to 15 to 20 seconds after contrast agent injection, the portal phase may refer to 50 to 70 seconds after contrast agent injection, and the delayed phase may refer to the phase 2 to 5 minutes after contrast agent injection.

Meanwhile, the CT image set may be an incomplete set of CT images with at least one missing phase.

The full-phase CT image set generation unit 200 synthesizes CT images with missing phases to generate a full-phase CT image set. That is, the full-phase CT image set generation unit 200 generates a full-phase CT image set, which is a complete CT image set, from an incomplete CT image set.

To this end, the full-phase CT image set generation unit 200 may include a generator 210 and a discriminator 220.

The generator 210 receives the incomplete CT image set and a target phase label.

Here, the target phase label has the form of an N-channel binary mask vector, and a component of the mask vector may have a specific value that distinguishes a missing phase from a non-missing phase. For example, the missing phase may be "0", and the missing phase may be "1", but the present disclosure is not limited thereto.

Meanwhile, an incomplete CT image set may be preprocessed based on the target phase label. More specifically, the incomplete CT image set may be preprocessed as shown in Equation 1 below to be correlated to a channel dimension of the target phase label.

$$\tilde{\mathcal{I}} = [I_1, I_2, 0, \ldots, I_N] \quad \text{[Equation 1]}$$

Here, "0" may denote a zero tensor with the form of $I_{i \neq m}$, and [.,.] may represent concatenation according to a channel dimension.

The image $\tilde{\mathcal{I}}$ preprocessed in this manner may be combined with a mask vector (m) and input to the generator 210 in a vector form of $[\tilde{\mathcal{I}}, m]$.

As a result, an index of the missing phase may be clearly expressed in the form of a mask vector, allowing the generator 210 to easily distinguish which phase is missing from the incomplete CT image set.

The generator 210 synthesizes the CT images with missing phases based on the received incomplete CT image set.

To this end, the generator 210 may be composed of a 3D U-NET architecture for synthesizing a 3D CT volume, and more specifically, composed of a 3×3×3 convolutional layer, strided convolution, a trilinear up-sampling layer, and skip connection. In particular, the generator 210 according to this embodiment may use trilinear interpolation instead of transverse convolution for upsampling, thereby preventing a checkboard artifact phenomenon in the synthesized 3D CT volume.

The discriminator 220 discriminates the CT image with missing phases synthesized by the generator 210 from an actual image.

To this end, the discriminator 220 uses strided 3D convolution to discriminate whether a local 3D patch is real or synthesized. At this time, the discriminator 220 may output a probability value indicating whether the CT image with missing phases synthesized by the generator 210 is an actual image.

Meanwhile, the generator 210 according to this embodiment may be trained to cause the discriminator 220 to make it difficult to discriminate the synthesized CT image with missing phases from the actual image.

More specifically, the generator 210 may be trained to minimize an adversarial loss $$\mathcal{L}_{adv}^{G}$$

defined as Equation 2 below in order to be trained to synthesize CT images $\hat{I}m = G(\tilde{\mathcal{I}}_m)$ with missing phases that are difficult to be discriminated by the discriminator 220.

$$\mathcal{L}_{adv}^{G} = \mathbb{E}_{\tilde{\mathcal{I}}_m}\left[(D(G(\tilde{\mathcal{I}}_m)) - 1)^2\right] \quad \text{[Equation 2]}$$

In addition, the discriminator 220 may be trained to minimize an adversarial loss $\mathcal{L}_{adv}^{D}$ defined as Equation 3 below in order to discriminate between an image $G(\mathcal{J}_m)$ generated by the generator 210 and a real image $I_m$.

$$\mathcal{L}_{adv}^{D} = \mathbb{E}_{I_m}\left[(D(I_m)-1)^2\right] + \mathbb{E}_{\mathcal{J}_m}\left[(D(G(\mathcal{J}_m)))^2\right] \quad \text{[Equation 3]}$$

Meanwhile, the generator 210 may be trained by further considering a reconstruction loss $\mathcal{L}_{rec}$ defined according to Equation 4 below in addition to the foregoing adversarial loss.

$$\mathcal{L}_{rec} = \mathbb{E}_{\mathcal{J}_m, I_m}\left[\|I_m - G(\mathcal{J}_m)\|_1\right] \quad \text{[Equation 4]}$$

That is, the reconstruction loss $\mathcal{L}_{rec}$ may be a loss that takes into account a distance in voxel units between an image $G(\mathcal{J}_m)$ synthesized by the generator 210 and a real image $I_m$.

The lesion-level feature extraction unit 300 extracts lesion features from the full-phase CT image set to classify a subtype of cancer. However, it may be difficult to classify the subtype of the cancer directly from an entire CT volume due to a small tumor size. Therefore, the lesion-level feature extraction unit 300 according to this embodiment extracts a feature map and a segmentation map from a full-phase CT image set, and extracts lesion-level features from the feature map and the segmentation map.

More specifically, as shown in FIG. 4, the lesion-level feature extraction unit 300 includes a segmentation map extraction unit 310 that extracts a segmentation map from a full-phase CT image set, a feature map extraction unit 320 that extracts a feature map from the full-phase CT image set, and a lesion-level feature calculation unit 330 that calculates lesion-level features from the extracted segmentation map and feature map.

First, the segmentation map extraction unit 310 extracts a segmentation map that predicts a probability that each voxel within each CT image belongs to a tumor region.

To this end, the segmentation map extraction unit 310 may be composed of a tumor segmentation network having a 3D U-Net architecture.

The 3D U-Net architecture, which is an architecture created based on an existing 2D U-Net, has an architecture that not only replaces the existing 2D U-Net including input, convolution, pooling, and upsampling processes, with 3D, but also improves performance by using a batch normalization technique. That is, the 3D U-Net architecture includes a plurality of 3×3×3 convolutional layers.

The tumor segmentation network having such a 3D U-Net architecture may extract a segmentation map through a process including a first step of receiving each CT image and applying convolution, batch normalization, and ReLU to extract a feature map, a second step of applying max pooling to reduce a size of the feature map, a third step of repeating the first and second steps N times, a fourth step of performing upconvolution on a final result that has been repeated N times using an upsampling ConvTranspose (deconvolution) technique, a fifth step of matching a dimension of a result obtained by upsampling with that of an N−1th result, a sixth step of connecting the N−1th result and a channel of the upsampling process with a skip-connection and then repeating a conv+BN+ReLU+upsampling operation, and a seventh step of restoring the dimension to its original state and then making the channels the same to obtain its result.

Meanwhile, the segmentation map extraction unit 310 may be trained by using a segmentation loss $\mathcal{L}_{seg}$ defined by Equation 5 below to extract a segmentation map having a well-defined tumor structure.

$$\mathcal{L}_{seg} = \mathbb{E}_{\hat{s},s}\left[1 - \frac{2\sum_{x\in X} s_x \hat{s}_x}{\sum_{x\in X} s_x^2 + \sum_{x\in X} \hat{s}_x^2}\right] \quad \text{[Equation 5]}$$

That is, the segmentation loss $\mathcal{L}_{seg}$ is a Dice loss, which quantifies a volume overlap between a predicted segmentation map $\hat{s}=S(G(\mathcal{J}_m))$ and a ground-truth segmentation map $s\in s$.

The feature map extraction unit 320 may extract a feature map from a CT image using a 3D convolutional neural network.

In particular, considering that the format of local texture is more helpful than the format of global volume statistics in order to characterize a lesion, the feature map extraction unit 320 according to this embodiment extracts a low-level feature map extracted from an initial convolutional layer constituting the tumor segmentation network. For example, the feature map extraction unit 320 may extract a feature map from the first two convolutional layers of the tumor segmentation network.

The lesion-level feature calculation unit 330 performs a masked average pooling operation on the feature map and the segmentation to calculate lesion-level features.

Here, the masked average pooling operation may be defined as Equation 6 below.

$$f^k = \frac{\sum_{x\in X} F_x^k \hat{s}_x}{\sum_{x\in X} \hat{s}_x} \quad \text{[Equation 6]}$$

Here, f is a lesion-level feature, $\hat{s}$ is a segmentation map, $\mathcal{X}$ is a set of all 3D spatial locations, and F is a feature map, which satisfies $k\in\{1, 2, \ldots, K\}$, where K refers to a dimension of the feature map.

The cancer subtype prediction unit 400 predicts a subtype of cancer based on the lesion-level features extracted from the lesion-level feature extraction unit 300.

The cancer subtype prediction unit 400 includes a concatenated feature unit 410 that generates concatenated lesion-level features and a classifier 420 that performs classification for a subtype of cancer based on the concatenated lesion-level features.

The concatenated feature unit 410 performs a concatenated operation on a plurality of lesion-level features extracted from each full-phase CT image set to generate concatenated lesion-level features.

The concatenated lesion-level features generated in this manner may be a NK-dimensional feature vector of $\mathcal{F}=[f_1, f_2, \ldots, f_N]$, where each component $f_i$ constituting the feature vector denotes lesion-level features acquired for an i-th CT image in the full-phase CT image set.

The classifier 420 passes the concatenated lesion-level features generated by the concatenated feature unit 410 through at least one fully-connected layer to perform classification for a subtype of cancer. As a result, a cancer subtype prediction result that focuses only on lesion-related features within a full-phase CT image set can be acquired.

Meanwhile, the classifier 420 may be trained in consideration of a cross-entropy loss defined as Equation 7 below.

Here, a loss for training of the classifier 420, which is a cross-entropy loss, may be defined as Equation 7 below.

$$\mathcal{L}_{cls} = \mathbb{E}_{\mathcal{J}_m^+, p}[-\log C(\mathcal{J}_m^+; p)] \quad \text{[Equation 7]}$$

Here, $$\mathcal{J}_m^+$$

is a full-phase image set $$\hat{p} = C(\mathcal{J}_m^+)$$

is a cancer subtype prediction result by the classifier 420, p∈p is a subtype classification, p is a set of cancer subtype labels for a training case, and $$C(\mathcal{J}_m^+; p)$$

represents a prediction probability for a target classification p.

Additionally, a full loss of the system 10 according to the present disclosure may be defined as Equation 8 below.

$$\mathcal{L} = \mathcal{L}_{adv}^G + \lambda_{rec}\mathcal{L}_{rec} + \lambda_{seg}\mathcal{L}_{seg} + \lambda_{cls}\mathcal{L}_{cls} \quad \text{[Equation 8]}$$

Here, $$\mathcal{L}_{adv}^G$$

is an adversarial loss of the generator 210, $\mathcal{L}_{rec}$ is a reconstruction loss of the generator 210, $\mathcal{L}_{seg}$ is a loss of the segmentation map extraction unit 310, $\mathcal{L}_{cls}$ is a loss of the classifier 420, $\lambda_{rec}$ is a weight for the reconstruction loss of the generator 210, $\lambda_{seg}$ is the weight for the loss of the segmentation map extraction unit 310, and $\lambda_{cls}$ represents a weight for the loss of the classifier 420.

That is, the integrated system 10 of the present disclosure may be trained to help cancer subtype classification by using a total loss as an objective function (full objective).

More specifically, the generator 210 may be trained to minimize an objective function, and the classifier 420 may be trained to minimize $\mathcal{L}_{cls}$, thereby ultimately allowing the generator 210 to generate CT images with missing phases that can lead to accurate prediction of a cancer subtype by the classifier 420.

FIGS. 5 and 6 are diagrams for explaining the cancer subtype classification performance of a system according to the present disclosure.

Figure 5A:
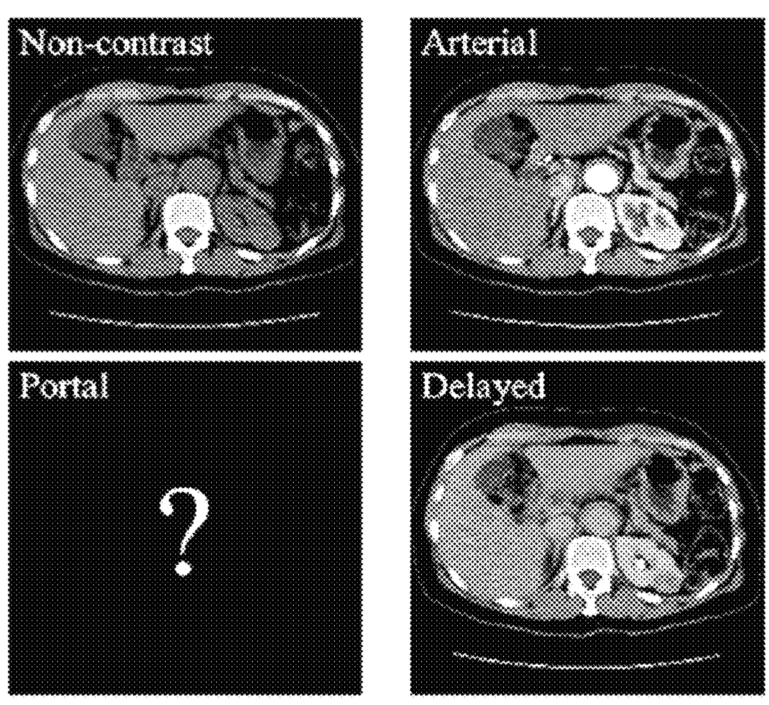
FIGS. 5A and 5B are CTs for quantitative comparison results of cancer subtype classification performances of an integrated system of the present disclosure.
Figure 5B:
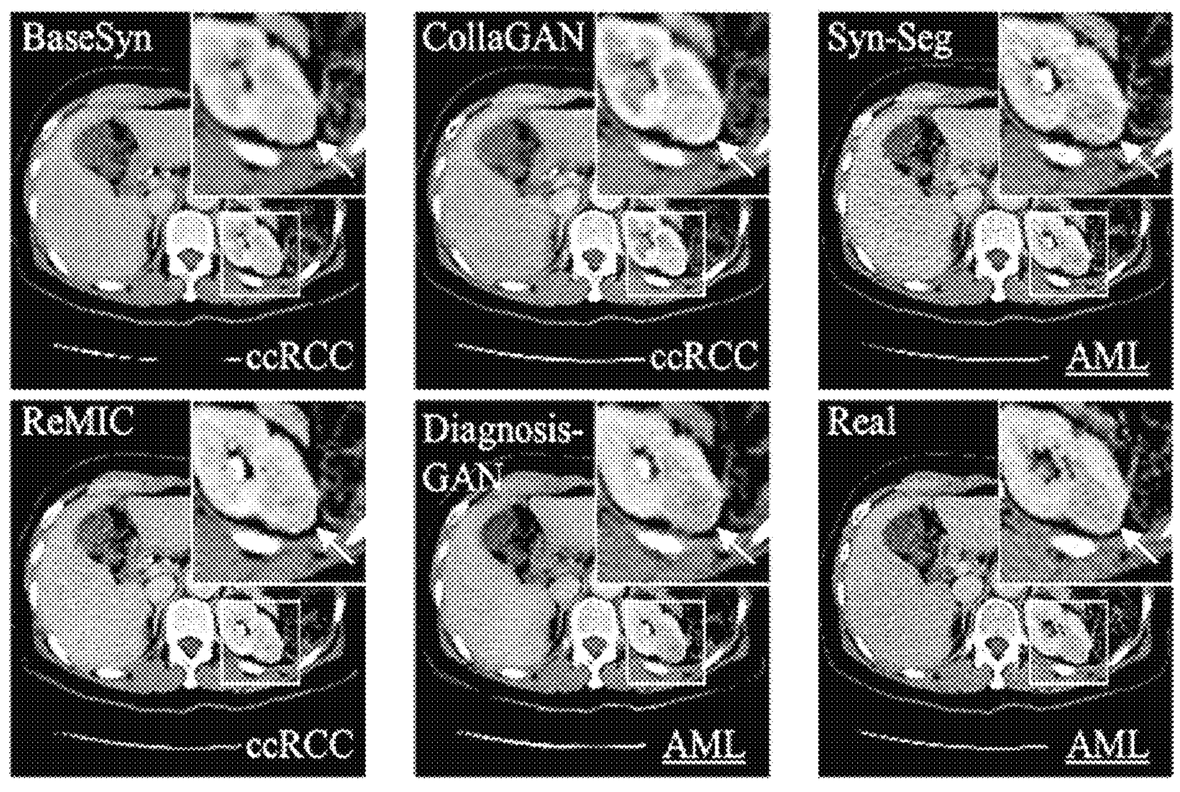

FIG. 5A shows an example in which a portal phase is missing, and FIG. 5B shows a Diagnosis-GAN image generated from a portal phase CT image to which the system according to the present disclosure is applied is shown along with other baselines, such as BaseSyn, CollaGAN, and Syn-Seg (Synthesis with Segmentation) and ReMIC.

According to FIG. 5B, it can be seen that a tumor region of the Diagnosis-GAN image is indicated by an arrow, wherein a result of cancer subtype classification using the system according to the present disclosure is more accurately predicted than those of cancer subtype classification through other baselines.

FIG. 6A is a table showing a result of classifying cancer subtypes using three actual CT images and one missing CT image, wherein it can be seen that the result of classifying cancer subtypes to which the system according to the present disclosure was applied showed an average AUC of 79.6%.

FIG. 6B is a table showing a result of classifying cancer subtypes using two actual CT images and two missing CT images in which the result of classifying cancer subtypes to which the system according to the present disclosure was applied showed an average AUC of 81.6%.

Figure 7:
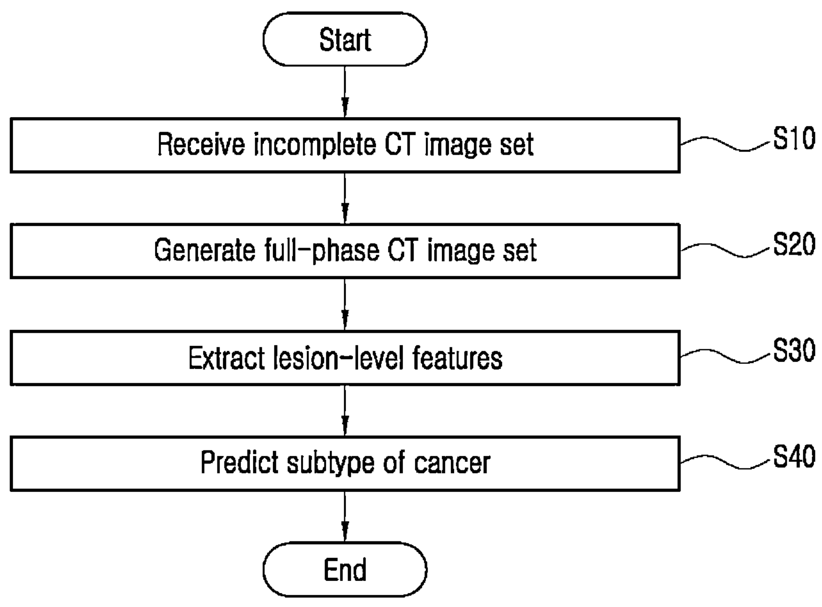
FIG. 7 is a diagram showing a flowchart of a cancer diagnosis method according to another embodiment of the present disclosure.

FIG. 7 is a diagram showing a flowchart of a cancer diagnosis method according to another embodiment of silver present disclosure.

The cancer diagnosis method according to this embodiment includes receiving an incomplete set of CT images (S10), generating a full-phase CT image set (S20), extracting lesion-level features (S30), and predicting a subtype of cancer (S40).

Meanwhile, the extracting of lesion level features (S30) may include extracting a segmentation map from the full-phase CT image set by a segmentation map extraction unit, extracting a feature map from the full-phase CT image set by a feature map extraction unit, and calculating lesion-level features from the extracted segmentation map and feature map by a lesion-level feature calculation unit.

More specifically, the segmentation map extraction unit may be configured with a tumor segmentation network to extract the segmentation map that predicts a probability that each voxel in the CT image belongs to a tumor region, the feature map extraction unit may extract a low-level feature map extracted from an initial convolutional layer constituting the tumor segmentation network, and the lesion-level feature calculation unit may perform masked average pooling on each of the extracted segmentation map and feature map to calculate the lesion-level features.

Meanwhile, the predicting of the subtype of the cancer (S40) may include performing, by a concatenated feature unit, a concatenated operation on the lesion-level features extracted from each full-phase CT image set to generate concatenated lesion-level features, and performing, by a classifier, classification for the subtype of the cancer based on the concatenated lesion-level features.

Here, the classifier may pass the concatenated lesion-level features through at least one fully-connected layer to perform classification for the subtype of the cancer.

Meanwhile, the full-phase CT image set generation unit may include a generator that synthesizes the CT images with missing phases based on the incomplete set of CT images, and a discriminator that discriminates the synthesized CT image with missing phases from an actual image, and the generator may be trained to cause the discriminator to make it difficult to discriminate the synthesized CT image with missing phases from the actual image.

Figure 8:
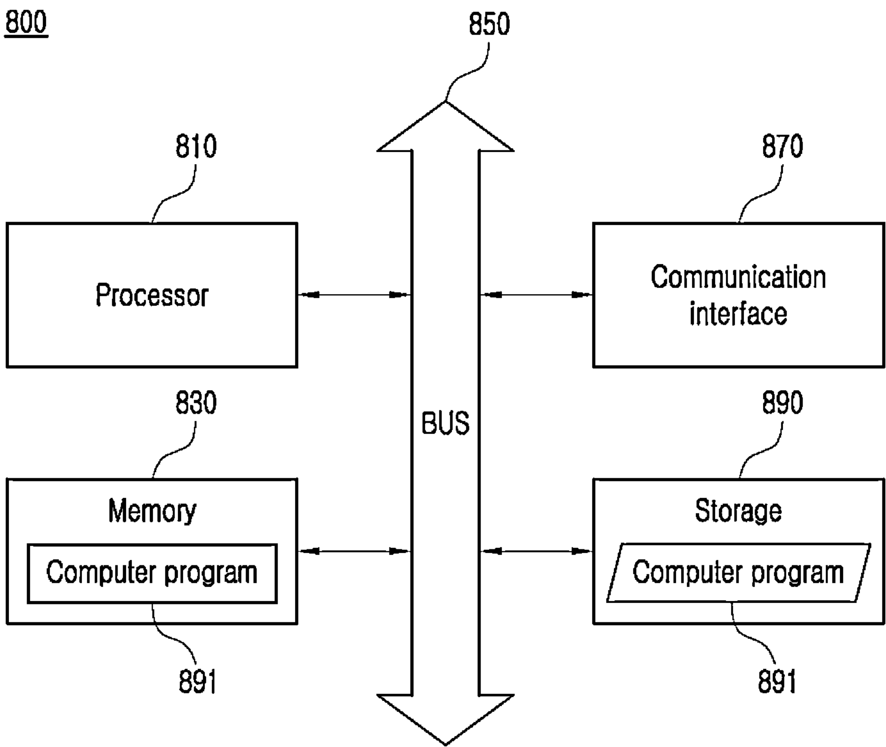
FIG. 8 is a diagram showing an exemplary computing device capable of implementing a device and/or a system according to various embodiments of the present disclosure.

FIG. 8 is a diagram showing an exemplary computing device 800 capable of implementing a device and/or a system according to various embodiments of the present disclosure.

The exemplary computing device 800 capable of implementing devices according to some embodiments of the present disclosure will be described in more detail with reference to FIG. 8.

The computing device 800 may include one or more processors 810, a bus 850, a communication interface 870, a memory 830 that loads a computer program 891 executed by the processor 810, and a storage 890 that stores the computer program 891. However, only elements related to embodiments of the present disclosure are shown in FIG. 8.

Accordingly, it will be appreciated by those skilled in the art that other general-purpose elements may be further included in addition to the elements shown in FIG. 8.

The processor 810 controls an overall operation of each component of the computing device 800. The processor 810 may include a central processing unit (CPU), a microprocessor unit (MPU), a micro controller unit (MCU), a graphic processing unit (GPU), or any type of processor 810 well known in the art of the present disclosure. In addition, the processor 810 may perform an operation on at least one application or program to execute a method according to embodiments of the present disclosure. The computing device 800 may include one or more processors 810. The computing device 800 may refer to artificial intelligence (AI).

The memory 830 stores various data, commands and/or information. The memory 830 may load one or more programs 891 from the storage 890 to execute methods according to embodiments of the present disclosure. The memory 830 may be implemented as a volatile memory such as RAM, but the technical scope of the present disclosure is not limited thereto.

The bus 850 provides a communication function between elements of the computing device 800. The bus 850 may be implemented as various types of buses, such as an address bus, a data bus, and a control bus.

The communication interface 870 supports wired and wireless Internet communication of the computing device 800. Additionally, the communication interface 870 may support various communication methods other than Internet communication. To this end, the communication interface 870 may include a communication module well known in the technical field of the present disclosure.

According to some embodiments, communication interface 870 may be omitted.

The storage 890 may non-temporarily store one or more programs 891 and various data.

The storage 890 may include a non-volatile memory such as a read only memory (ROM), an erasable programmable ROM (EPROM), an electrically erasable programmable ROM (EEPROM), a flash memory, or the like, a hard disk, a removable disk, and a type of computer-readable recording medium widely known in the art to which the present disclosure pertains.

The computer program 891 may include, when loaded into the memory 830, one or more commands that cause the processor 810 to perform methods/operations according to various embodiments of the present disclosure. That is, the processor 810 may perform methods/operations according to various embodiments of the present disclosure by executing the one or more commands.

While the preferred embodiments of the present disclosure have been shown and described above, it will be of course understood by those skilled in the art that various modifications may be made without departing from the gist of the disclosure as defined in the following claims, and it is to be noted that those modifications should not be understood individually from the technical concept and prospect of the present disclosure.

What is claimed is:

1. A cancer diagnosis system that performs cancer diagnosis from an incomplete set of CT images having at least one missing phase, the cancer diagnosis system comprising:

an input unit that receives the incomplete set of CT images;

a full-phase CT image set generation unit that synthesizes CT images for the at least one missing phase to generate a full-phase CT image set;

a lesion-level feature extraction unit that extracts a feature map and a segmentation map from the full-phase CT image set, and extracts lesion-level features from the feature map and the segmentation map; and a cancer subtype prediction unit that predicts a subtype of cancer based on the extracted lesion-level features, wherein the lesion-level feature extraction unit comprises:

a segmentation map extraction unit that extracts the segmentation map from the full-phase CT image set;

a feature map extraction unit that extracts the feature map from the full-phase CT image set; and a lesion-level feature calculation unit that calculates the lesion-level features from the extracted segmentation man and the extracted feature map, wherein the segmentation map extraction unit is configured with a tumor segmentation network to extract the segmentation map that predicts a probability that each voxel in each CT image of the full-phase set belongs to a tumor region, wherein the feature map extraction unit extracts a low-level feature map extracted from an initial convolutional layer constituting the tumor segmentation network, wherein the lesion-level feature calculation unit performs masked average pooling on each of the extracted segmentation map and the extracted feature map to calculate the lesion-level features, wherein the full-phase CT image set generation unit comprises:

a generator that synthesizes the CT images for the at least one missing phase based on the incomplete set of CT images; and a discriminator that discriminates the synthesized CT image for the at least one missing phase from an actual image, wherein the generator is trained to generate the synthesized CT image for the at least one missing phase to be similar to the actual image such that discrimination by the discriminator is difficult.

2. The cancer diagnosis system of claim 1, wherein the cancer subtype prediction unit comprises:

a concatenated feature unit that performs a concatenated operation on the lesion-level features extracted from each CT image of the full-phase CT image set to generate concatenated lesion-level features; and a classifier that performs classification for the subtype of the cancer based on the concatenated lesion-level features.

3. The cancer diagnosis system of claim 2, wherein the classifier passes the concatenated lesion-level features through at least one fully-connected layer to perform the classification for the subtype of the cancer.

4. A cancer diagnosis method that performs cancer diagnosis from an incomplete set of CT images having at least one missing phase, the cancer diagnosis method comprising:

receiving, by an input unit, the incomplete set of CT images;

synthesizing, by a full-phase CT image set generation unit, CT images for the at least one missing phase to generate a full-phase CT image set;

extracting, by a lesion-level feature phase unit, a feature map and a segmentation map from the full-phase CT image set, and extracting lesion-level features from the feature map and the segmentation map; and predicting, by a cancer subtype prediction unit, a subtype of cancer based on the extracted lesion-level features, wherein the extracting the feature map and the segmentation map and the extracting the lesion-level features comprises:

extracting by a segmentation map extraction unit the segmentation map from the full-phase CT image set;

extracting by a feature map extraction quit the feature map from the full-phase CT image set; and calculating, by a lesion-level feature calculation unit, the lesion-level features from the extracted segmentation map and the extracted feature map, wherein the segmentation map extraction unit is configured with a tumor segmentation network to extract the segmentation map that predicts a probability that each voxel in each CT image of the full-phase CT image set belong to a tumor region, wherein the feature map extraction unit extracts a low-level feature map extracted from initial convolutional layer constituting the tumor segmentation network, wherein the lesion-level feature calculation unit performs masked a ze pooling ne of the extracted segmentation map and the extracted feature map to calculate the lesion-level feature, wherein the full-phase image set generation unit comprises:

a generator that synthesizes the CT images for the at least one missing phase based on the incomplete set of CT images, and discriminator that discriminates synthesized CT image for the at least one missing phase from actual image, wherein the generator is trained to generate the synthesized CT image for the at least one missing phase to be similar to the actual image such that discrimination by the discriminator is difficult.

5. The cancer diagnosis method of claim 4, wherein the predicting of the subtype of the cancer comprises:

performing, by a concatenated feature unit, a concatenated operation on the lesion-level features extracted from each CT image of the full-phase CT image set to generate concatenated lesion-level features; and performing, by a classifier, classification for the subtype of the cancer based on the concatenated lesion-level features.

6. The cancer diagnosis method of claim 5, wherein the classifier passes the concatenated lesion-level features through at least one fully-connected layer to perform the classification for the subtype of the cancer.

* * * * *